United States Patent [19]

Ogawa

[11] Patent Number: 4,844,913

[45] Date of Patent: Jul. 4, 1989

[54] DIETARY PRODUCT CONTAINING GLUCOMANNAN POWDER AND METHOD FOR PREPARING

[75] Inventor: Ikuzo Ogawa, Kanagawa, Japan

[73] Assignees: Kabushiki Kaisha Maruzen Shokuhin; Kabushiki Kaisha Sokensha, both of Japan

[21] Appl. No.: 194,211

[22] Filed: May 16, 1988

[30] Foreign Application Priority Data

May 20, 1987 [JP] Japan ................................. 62-121026

[51] Int. Cl.$^4$ ........................... A23L 1/20; A23L 1/10
[52] U.S. Cl. ......................................... 426/18; 426/46; 426/52; 426/63; 426/804; 426/634; 426/648
[58] Field of Search ..................... 426/46, 63, 52, 804, 426/18, 573, 634, 648

[56] References Cited

U.S. PATENT DOCUMENTS 4,379,173  4/1983  Masuyama ........................... 426/549
4,393,086  7/1983  Masuyama ........................... 426/804

*Primary Examiner*—Marianne Cintirs
*Attorney, Agent, or Firm*—Wegner & Bretschneider

[57] ABSTRACT

Disclosed is a dietary foodstuff comprising: (a) glucomannan powder; (b) soybean powder, at 30–100% by weight glucomannan powder, that has been reacted with a protein hydrolysis enzyme, at 5–15% by weight soybean powder; (c) bittern, at 0.5–3% by weight glucomannan powder; (d) refined rice flour, at 0.5–7% by weight glucomannan powder; (e) water, at 10–70 times by weight glucomannan powder; and (f) glucomannan powder coagulant, at 5–10% by weight glucomannan powder, soybean flour, enzyme, bittern, and rice flour.

9 Claims, No Drawings

DIETARY PRODUCT CONTAINING GLUCOMANNAN POWDER AND METHOD FOR PREPARING

This invention relates to processed foodstuffs containing konjak and their manufacturing processes. "Konjak" is a name for Japanese food comprising glucomannan, which can be obtained from the "devil's tongue" root, which belongs to the family *Colocasia antiquorum*.

It is common knowledge that the number of obese people is presently increasing. This increase is probably due to improvements in economic and food conditions and changes in mode of living. It is considered that corpulence is undesirable for maintaining one's health and a graceful figure.

In recent years, konjak has been known to be a healthful foodstuff and has received much attention in Japan as a dietary food substitute for appetizing foods, because glucomannan, which is a major constituent of konjak, gives a feeling of fullness without many calories.

Furthermore, it is known that konjak is helpful in protecting individuals from cancer of the rectum or the colon, because konjak passes through the intestines without digestion while absorbing harmful surplus materials and cleaning the intestines.

But, conventional konjak is not suitable for eating as a principal food, such as rice or noodles, because it is difficult to chew, has a rough feeling to the tongue, and an unpleasant taste.

Heretofore, the prior art has tried to remove the unpleasant taste of konjak and increase its use by adding it to various foods, for example, vegetables, soybean powder, flour, cornstarch and so on.

However, these foods made no more than a small change in the taste of konjak. Also, for practical consumption, such foods must be cooked in the same way as usual rice or noodles. Furthermore, the taste and resistance to the teeth as well as the external appearance and form of such foods should be similar to usual rice or noodles.

One conventionally processed foodstuff made from konjak, when mixed with vegetables, has the same smell and feeling of meal compared with pure konjak, even though it contains some grains or some small pieces of vegetables.

Another conventionally processed konjak foodstuff, when mixed with soybean powder, is white compared to pure konjak, and has a different feeling of meal. However, the konjak foodstuff is only useful as pudding, tofu, or a pot-steamed hotchpotch. The texture and taste of rice or noodles cannot be duplicated using this foodstuff. Therefore, although soybean odor mixed with the smell of konjak to remove konjak odor, substitute foods for rice or noodles could not be obtained, because of the texture and taste of these foods effected by use of soybeans.

The suggestion has been made to mix flour or cornstarch, which was used usually as starch, with konjak, in order to get the same taste and texture of rice or noodles. However, when mixed with konjak, starch does not dissolve, and separated starch particles adhere to the surface of the konjak, or float in the solution mix, therefore good feeling of meal and good external appearance are not obtained. Specifically, such a foodstuff cannot be put on the market. Furthermore, mixing starch with konjak makes the konjak nonelastic, so it cannot be set into foods such as noodles.

Modified glucomannan powder contained in konjak is disclosed in U.S. Pat. Nos. 4,379,173 and 4,393,086. U.S. Pat. No. 4,379,173 disclosed a process for preparing glucomannan-containing biscuits. However, such biscuits are inedible as a principal food. Accordingly, the present invention is a dietary foodstuff comprising (a) glucomannan powder; (b) soybean powder at 30–100% by weight glucomannan powder reacted with a protein hydrolysis enzyme at 5–15% by weight soybean powder; (c) bittern at 0.5–3% by weight glucomannan powder; (d) refined rice flour at 0.5–7% by weight glucomannan powder; (e) water, at 10–70 times by weight glucomannan powder; and (f) glucomannan powder coagulant at 5–10% by weight of the glucomannan powder, soybean powder, enzyme, bittern, and rice flour. The present invention is also a process for making a dietary foodstuff comprising the steps of: (a) combining a protein hydrolysis enzyme and an aqueous solution of soybean powder and allowing the mixture to stand; (b) combining the mixture from step (a) with an aqueous solution of rice flour and an aqueous solution of bittern; (c) combining the resultant mixture of step (b) with glucomannan powder and allowing the mixture to stand; (d) kneading the resulting mixture of step (c); and (e) combining the kneaded mixture with an aqueous solution of glucomannan powder coagulant; wherein, based on the weight of glucomannan powder, soybean powder is used at 30–100%, rice flour is used at 0.5–7% by weight, and bittern is used at 0.5–3%, the enzyme is used at 5–15% by weight of the soybean powder, the coagulant is present at 5–10% by weight of glucomannan powder, bittern, rice flour, soybean powder, and coagulant, and water is used at 25–70 times by weight powder.

Glucomannan (konjak) powder useful in accordance with the present invention is obtained from known processes, such as disclosed in the heretofore mentioned U.S. Pat. No. 4,393,086, incorporated herein by reference. Preferably, the glucomannan powder has a particle size between about 80 and 250 mesh.

Useful soybean powder is obtained by known processes, such as removing the skin from the soybean and reducing the bean to powder by steaming. Preferably the soybean powder particle size is 100–300 mesh, and the amount of soybean powder is 30–60% by weight of konjak powder. Useful protein hydrolysis enzymes include bromelain, trypsin, and chymotrypsin. Bromelain is preferred.

Useful konjak coagulants are well known alkalai compounds, including calcium hydroxide, sodium carbonate, potassium carbonate, as well as calcium obtained from calcinated eggshells. The amount of coagulant is preferably 6–10% by weight of the total of bittern, rice flour, soybean powder, glucomannan powder, and enzyme.

Refined rice flour is produced by well known methods, such as mixing with water and reducing the mix to particulate form. Preferably, the particle size of the rice flour is between about 100 and 300 mesh.

Bittern is the well known solution of bromides, magnesium, and calcium salts that remains after sodium chloride has been crystallized by concentrating sea water or brines.

Preferably, the soybean powder is allowed to stand in water for about 5–30 minutes before adding the enzyme. The enzyme and soybean powder solution are preferably stirred for about 5-20 minutes, and more preferably thereafter allowed to stand for about 5-30 minutes. To the resultant mixture is then added the bittern and rice flour solutions, which mixture is preferably stirred for another 5-30 minutes, then allowed to preferably stand for about 30 minutes to 2 hours.

The amount of coagulant used depends on the firmness desired for the finished end product. The more coagulant added, the harder the foodstuff becomes, 5% coagulant giving a very soft material and 10% coagulant giving a very hard material very quickly. Accordingly, if for example, hard noodles are desired, the kneaded material must be passed through a mesh promptly after the coagulant is added. Likewise, if a solid bar of foodstuff is desired, the material plus coagulant must be placed in the desired container before it sets. After setting, the hardened foodstuffs can be softened by heating in water between 60°-75° C. for about 5-10 minutes. Packaging of the resoftened material should be done by placing the material in hot water (about 60° C.) into the packaging and then allowing it to cool at ambient temperatures.

Cooking noodles made from the konjak foodstuff according to the present invention by the same way of cooking chinese noodles results in noodles that are equal to regular noodles made from wheat flour, from the point of view, for example, of external appearance, color, feeling of meals, (ease of chewing, the feeling by tongue, etc.), and smell. Many individuals cannot tell the difference between regular noodles and noodles made from the foodstuff of the present invention.

Furthermore, in a hotchpotch containing the noodles of konjak according to the present invention, after cutting in small pieces, with whole rice, the konjak "rice" cannot be distinguished from the whole rice by many individuals.

Finally, in processed foodstuffs containing konjak according to the present invention, there are no floating particles of soybean powder or refined rice flour, nor are such particles adhered to the surface of the foodstuffs, as in the case of prior art konjak/soybean powder foodstuffs.

No individual pieces of rice or soybean flour are found in the foodstuffs of the present invention, and are were no floating pieces of rice or soybean when the foodstuffs are placed in boiling water.

After keeping the processed foodstuffs of konjak according to the present invention for 1 year, no changes in smell and taste are observed, nor is there separation into konjak powder, rice flour, or soybean powder observed.

In order to more fully describe the present invention, the following non-limiting example is provided.

EXAMPLE 15.7 kg of soybean powder is put into 50 l of water (30°-50° C.) and stirred vigorously until the solution becomes like soybean milk. Stirring is vigorous to avoid formation of a powdery ball.

1.9 kg of protein hydrolysis enzyme (bromelain obtained from pineapple) and 170 ml of yellow food color (Carotin 9400-S) are added to the milky solution, and the mixture is stirred for 5 minutes and left to stand for 30 minutes to obtain "the first solution."

240 g of natural bittern is dissolved in 10 l of water (30° C.), and the solution is called "the second solution."

240 g of refined rice flour is dissolved into 10 l of water (30° C.), and the solution is called "the third solution."

Mixing and stirring the first solution, the second solution, and the third solution in 730 l of water (30° C.) is performed for about 3 minutes. 16 kg of konjak powder is dissolved in this mixture by adding gradually at the rate of 5 kg/min. The resulting mixture is stirred for 15-20 minutes until the viscosity of konjak powder increases, and then left to stand for about 90 minutes.

1.8 kg of the konjak coagulant (calcium hydroxide) is dissolved in 100 l of water (30° C.).

The material that has been left to stand for 90 minutes is placed into a kneading machine, and kneaded for $5 \approx 10$ seconds by a fan operating at 380 revolutions/min. During this time, the coagulant dissolved in water is mixed into the material. The material sets almost immediately, becoming very firm.

What is claimed is:

1. A dietary foodstuff comprising:
   (a) glucomannan powder;
   (b) soybean powder, at 30-100% by weight glucomannan powder, that has been reacted with a protein hydrolysis enzyme, at 5-15% by weight soybean powder;
   (c) bittern, at 0.5-3% by weight glucomannan powder;
   (d) refined rice flour, at 0.5-7% by weight glucomannan powder;
   (e) water, at 10-70 times by weight glucomannan powder; and
   (f) glucomannan powder coagulant, at 5-10% by weight glucomannan powder, soybean powder, enzyme, bittern, and rice flour.

2. The foodstuff of claim 1 wherein the protein hydrolysis enzyme is bromelain.

3. The foodstuff of claim 1 wherein the soybean powder is present at 30-60% by weight glucomannan powder.

4. The foodstuff of claim 1 wherein the coagulant is present at 6-10% by weight glucomannan powder, soybean powder, rice flour, enzyme, and bittern.

5. The foodstuff of claim 1 wherein water is present at 25-70 times by weight glucomannan powder.

6. A process for making a dietary foodstuff comprising the steps of:
   (a) combining a protein hydrolysis enzyme and an aqueous solution of soybean powder and allowing the mixture to stand;
   (b) combining the mixture from step (a) with an aqueous solution of rice flour and an aqueous solution of bittern;
   (c) combining the resultant mixture of step (b) with glucomannan powder and allowing the mixture to stand;
   (d) kneading the resulting mixture of step (c); and
   (e) combining the kneaded mixture with an aqueous solution of glucomannan coagulant;
wherein, based on the weight of glucomannan powder, the soybean flour is used at 30-100%, the rice flour is used at 0.5-7%, and the bittern is used at 0.5-3%, the enzyme is used at 5-15% by weight soybean powder, the coagulant is present at 5-10% by weight glucomannan powder, bittern, rice flour, soybean powder, and coagulant, and water is used at 10-70 times by weight of glucomannan powder.

7. The process of claim 6 wherein soybean powder is used at 30-60% by weight glucomannan powder.

8. The process of claim 6 wherein the coagulant is used at 6-10% by weight glucomannan powder, rice flour, soybean powder, bittern, and enzyme.

9. The process of claim 6 wherein water is used at 25-70 times by weight glucomannan powder.

* * * * *